United States Patent
Jeong (10) Patent No.: US 11,406,528 B2
(45) Date of Patent: Aug. 9, 2022

(54) COLD AND HOT THERMAL TREATMENT DEVICE

(71) Applicant: Industrial Cooperation Foundation Chonbuk National University, Jeonju-si (KR)

(72) Inventor: Hwan Jeong Jeong, Jeonju-si (KR)

(73) Assignee: Industrial Cooperation Foundation Chonbuk National University, Jeonju-si (KR)

(*) Notice: Subject to any disclaimer, the term of this patent is extended or adjusted under 35 U.S.C. 154(b) by 205 days.

(21) Appl. No.: 16/065,814

(22) PCT Filed: Jun. 26, 2017

(86) PCT No.: PCT/KR2017/006720
§ 371 (c)(1),
(2) Date: Jun. 24, 2018

(87) PCT Pub. No.: WO2019/004491
PCT Pub. Date: Jan. 3, 2019

(65) Prior Publication Data
US 2021/0196504 A1    Jul. 1, 2021

(51) Int. Cl.
*A61F 7/00* (2006.01)
*F25B 21/04* (2006.01)

(52) U.S. Cl.
CPC ............... *A61F 7/00* (2013.01); *F25B 21/04* (2013.01); *A61F 7/0085* (2013.01); *A61F 2007/0036* (2013.01); *A61F 2007/0045* (2013.01); *A61F 2007/0071* (2013.01);
(Continued)

(58) Field of Classification Search
CPC ...... A61F 2007/0036; A61F 2007/0045; A61F 2007/0071; A61F 2007/0075; A61F 2007/0086; A61F 2007/0096; A61F 7/00; A61F 7/0085; A61H 33/06
See application file for complete search history.

(56) References Cited

U.S. PATENT DOCUMENTS

2002/0107543 A1*  8/2002  Voznesensky ..... A61N 1/36017
                                          607/3
2016/0022477 A1*  1/2016  Schaefer ................. A61F 7/00
                                          607/104

FOREIGN PATENT DOCUMENTS

KR          200167798 Y1      2/2000
KR        20060098529 A       9/2006
(Continued)

OTHER PUBLICATIONS

International Search Report issued in related application No. PCT/KR2017/006720 dated Feb. 23, 2018.

*Primary Examiner* — Tigist S Demie
(74) *Attorney, Agent, or Firm* — Troutman Pepper Hamilton Sanders LLP; Ryan A. Schneider (57) ABSTRACT

The present disclosure relates to a cold and hot thermal treatment device. Hot heat and cold heat are produced by a heat production unit and are periodically and repeatedly transferred to a heat transfer unit that is in contact with a human body such that a temperature is not suddenly changed but is gradually changed. Thus, the device may be used when diagnosing whether vascular reactivity is maintained in corresponding hands and feet, may generate a temperature stimulus, and may repeatedly perform the temperature stimulus, thereby improving the vascular reactivity.

17 Claims, 9 Drawing Sheets

(52) U.S. Cl.
CPC ................ *A61F 2007/0075* (2013.01); *A61F 2007/0086* (2013.01); *A61F 2007/0096* (2013.01)

(56) References Cited

FOREIGN PATENT DOCUMENTS

| KR | 20100129837 | A  | 12/2010 |
|----|-------------|----|---------|
| KR | 101667320   | B1 | 10/2016 |

\* cited by examiner

COLD AND HOT THERMAL TREATMENT DEVICE

TECHNICAL FIELD

The present disclosure relates to a cold and hot thermal treatment device, and more particularly, to a cold and hot thermal treatment device for identifying and improving vascular reactivity of hands and feet.

BACKGROUND ART

Vascular reactivity refers to regulation of body's metabolic processes through expansion and contraction of blood vessels to adapt to changes in a surrounding environment, such as hands and feet, which are the most sensitive parts of a body.

In general, there are people around us, who feel cold or warm on hands or feet. Pain and swelling may occur when you feel that coldness is getting worse and worse. In addition, when a patient has metabolic diseases such as diabetes, the patient will have neuropathy or vasculopathy as complications at a peripheral site.

These symptoms and diseases should ultimately be resolved by finding an underlying cause. However, in some cases, the underlying cause is not found, and even if the underlying cause is known, it may not be easy to resolve the underlying cause, which is like diabetes. Further, it is necessary to carry out realistic treatment for an area where a present symptom exists.

When the complications in the peripheral site are caused by the metabolic diseases or when cause of diseases cannot be determined accurately but the patient has symptoms called hand and foot coldness, since circulation through a peripheral blood vessel is poor, symptoms occur in a corresponding site. That is, since the vascular reactivity is broken, a blood vessel cannot be expanded when the blood vessel should be expanded, and the blood vessel cannot be relaxed when the blood vessel should be relaxed. Further, when platinum-based or taxane-based neurotoxic anticancer drugs are administrated to a patient receiving anticancer therapy through drugs, neuropathy or vasculopathy, such as numbed peripheral area or decreased sensation, occurs as a complication.

Even when the vascular reactivity is broken by the metabolic diseases, a complication occurs. Further, direct and active treatment of a site where the complication is to be delayed in addition to treatment of the metabolic diseases themselves is required to delay a process in which diseases are progressed. Vascular reactivity recovery training is one of treatment processes.

When a change in an external environment is induced to identify and correct maintenance of the vascular reactivity, the most important external environment is the temperature. A change in a temperature causes expansion and contraction of a microvessel to induce homeostasis of a body.

In terms of a physiological aspect of a human body, the human body gradually adapts to external changes. A sudden change in a temperature is an attentive form as the change may disrupt the physiological adaptation process in maintaining homeostasis. The sudden change is a situation in which homeostasis of even normal people may be disturbed, and thus is a more dangerous condition to those who may have the above-described abnormal neurovascular disease.

Required are a device that may identify whether the vascular reactivity is maintained or broken in the corresponding hand or foot and a device that may recover the vascular reactivity.

DISCLOSURE

Technical Problem

The present disclosure is conceived to solve the above-described problems and provides a cold and hot thermal treatment device in which hot heat and cold heat are produced by a heat production unit and are periodically and repeatedly transferred to a heat transfer unit that is in contact with a human body such that a temperature is not suddenly changed but is gradually changed. Thus, the device may be used when diagnosing whether vascular reactivity is maintained in corresponding hands and feet, may generate a temperature stimulus, and may repeatedly perform the temperature stimulus, thereby improving the vascular reactivity.

Technical Solution

To achieve the above-described aspect, a cold and hot thermal treatment device may include: a heat production unit configured to produce hot heat and cold heat; a power source electrically connected to the heat production unit to supply electric power; a heat transfer unit configured to transfer heat produced by the heat production unit to a target portion that is in contact with a human body; and a controller configured to control the heat production unit to repeatedly and alternately generate the hot heat and the cold heat according to a set period, to perform a control such that a temperature is gradually increased to a predetermined maximum temperature and is gradually decreased to a predetermined minimum temperature according to a constant rate for temperature increase/decrease, and to perform a control such that after the temperature reaches the maximum temperature and the minimum temperature, the temperature is maintained for a predetermined time period.

The cold and hot thermal treatment device may further include a digital thermometer and a timer.

An insulator may be installed in a heat transfer passage provided between the heat production unit and the heat transfer unit.

A temperature measuring sensor may be further installed at a distal end of the heat transfer unit, which is in contact with a human body.

The hot heat produced by the heat production unit may be produced by any one of a thermoelectric element, an electrothermal wire, and a vortex tube.

The cold heat produced by the heat production unit may be produced by any one of a thermoelectric element, a compressor, a refrigerant, and an evaporator, and liquid nitrogen and dry ice, and a vortex tube.

The heat transfer unit may be a box-shaped or cover-shaped sealed space part which is selectively opened and in which a part or a lower half part of a human body is accommodated.

Advantageous Effects

To solve the above-described problems, a temperature stimulus that may be used when diagnosing whether vascular reactivity is maintained in a corresponding hand or foot or is broken is generated and a gradually heated or cooled temperature stimulus is repeatedly performed so that a vascular exercise to a stimulus is consistently performed. Accordingly, the disease may be treated through rehabilitation for the vascular reactivity.

MODES OF THE INVENTION

Hereinafter, embodiments of the present disclosure will be described in detail with reference to the accompanying drawings. First, it should be noted that when components in the drawings are designated by reference numerals, the same components have the same reference numerals as far as possible even though the components are illustrated in different drawings. Further, in description of the present disclosure, when it is determined that detailed descriptions of well-known configurations or functions make the subject matter of the present disclosure unclear, the detailed descriptions will be omitted. Further, although exemplary embodiments of the present disclosure will be described below, the technical spirit of the present disclosure is not limited thereto, and may be implemented by those skilled in the art.

Figure 1:
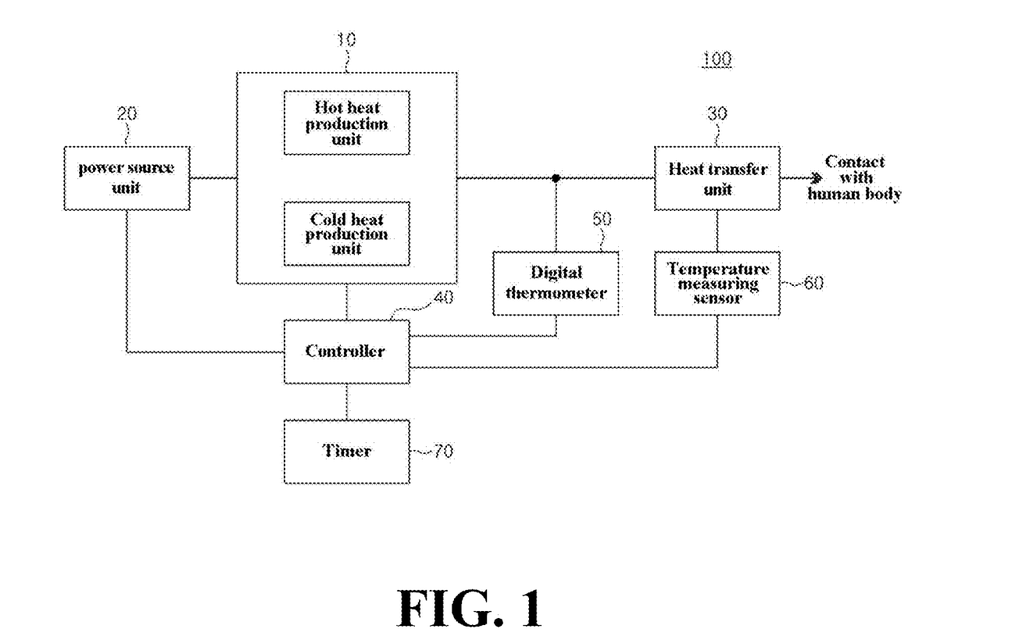
FIG. 1 is a view schematically illustrating a configuration of a cold and hot thermal treatment device according to the present disclosure.
Figure 2:
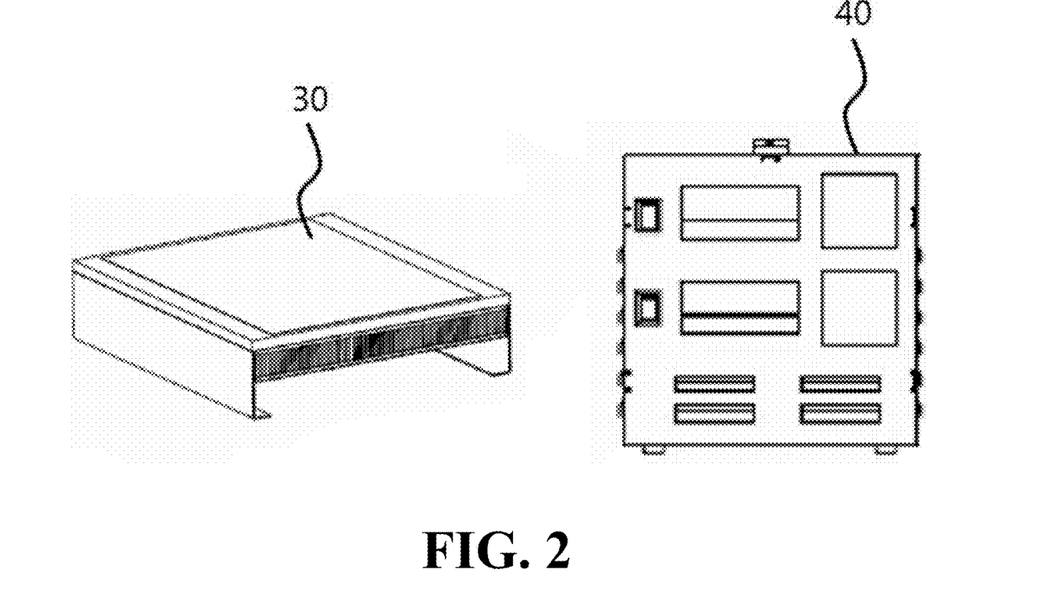
FIGS. 2 to 4 are views illustrating an outer appearance of the cold and hot thermal treatment device according to the present disclosure.
Figure 3:
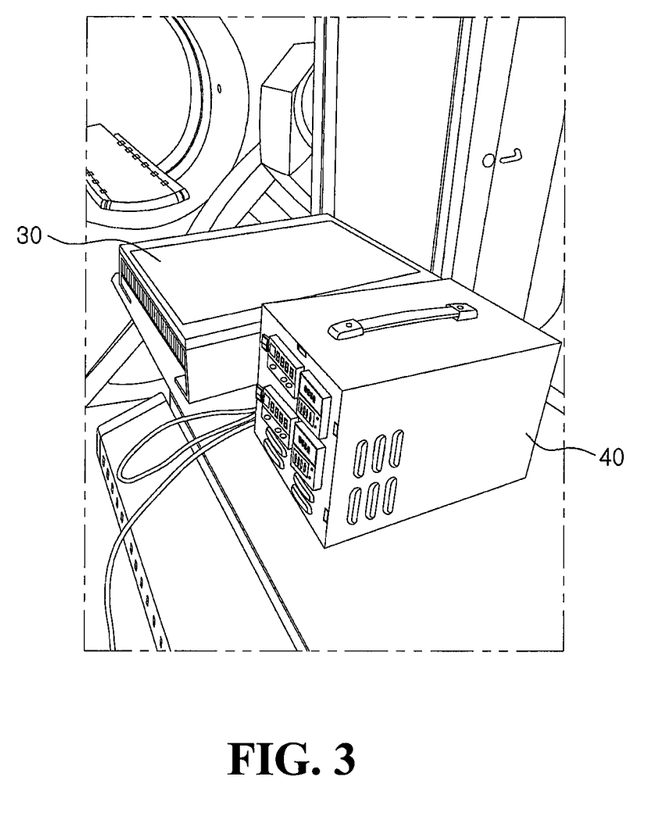
Figure 4:
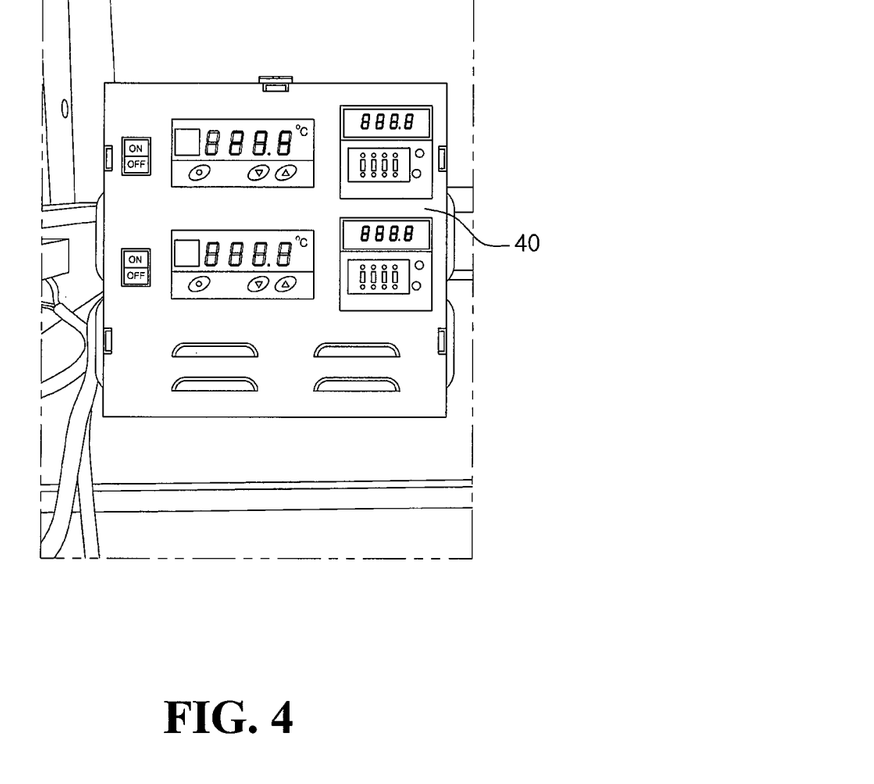

FIG. 1 is a view schematically illustrating a configuration of a cold and hot thermal treatment device according to the present disclosure, and FIGS. 2 to 4 are views illustrating an outer appearance of the cold and hot thermal therapy device according to the present disclosure.

As illustrated in FIGS. 1 to 4, a cold and hot thermal treatment device 100 according to the present disclosure is a treatment device configured to perform a repeated control such that hot heat and cold heat are alternately generated according to a set time and a set temperature, to transfer a temperature stimulus to a hand and a foot of a user, to help to identify whether temperature responsiveness for the temperature stimulus is maintained in the corresponding hand or foot, and to improve broken vascular reactivity of a patient. The cold and hot thermal treatment device 100 includes a heat production unit 10, a power source unit 20, a heat transfer unit 30, and a controller 40. Further, the cold and hot thermal treatment device 100 further includes a digital thermometer 50 and a timer 70.

The heat production unit 10 is configured to produce hot heat and cold heat, and the power source unit 20 may be a transformer (SNIPS) electrically connected to the heat production unit 10 to supply electric power and convert a current of a direct current (DC) power source.

It is preferable that the heat transfer unit 30 transfers heat produced by the heat production unit 10 to a target portion that is in contact with a human body, an insulator is installed in a heat transfer passage provided between the heat production unit 10 and the heat transfer unit 30, and the heat transfer unit 30 may be formed of, for example, metal such that the heat produced by the heat production unit 10 may be conducted well to the target portion that is in contact with the human body. Further, a temperature measuring sensor 60 is further installed at a distal end of the heat transfer unit 30, which is in contact with a human body.

The controller 40 controls the heat production unit 10 to alternately generate the hot heat and the cold heat according to a set time and a set temperature. That is, when it is determined through the digital thermometer 50 that a temperature reaches the set temperature, the controller 40 may maintain the temperature by adjusting the heat production unit 10 and may perform counting by setting a specific time through the timer 70.

As illustrated in FIG. 4, in the controller 40, two digital thermometers 50 and two timers 70 installed on the front surface of a body of the cold and hot thermal treatment device 100 are connected to each other, and the digital thermometers 50 convert the size of the heat produced by the heat production unit 10 into degrees Celsius and display the size of the heat.

Since a specific limitation value may be set, the digital thermometer 50 may be used to display a temperature such that the heat produced by the heat production unit 10 does not deviate from the set limitation value.

The timer 70 is connected to the controller 40 to set a specific value. After a set value elapses, the controller 40 changes a direction of a current to repeatedly switch an operation of the heat production unit 10 from the hot heat to the cold heat or from the cold heat to the hot heat.

As illustrated in FIGS. 2 to 4, in the above-configured cold and hot thermal treatment device 100 according to the present disclosure, it is preferable that a thermoelectric element of the heat production unit 10 is installed in a central portion of the heat transfer unit 30 by using at least one prototype Peltier device.

A body of the cold and hot thermal treatment device 100 according to the present disclosure includes a display unit configured to display a measured temperature and a set temperature together with the controller 40, a power switch, a plurality of operation buttons, and a fan for improving efficiency of the thermoelectric element.

Figure 5:
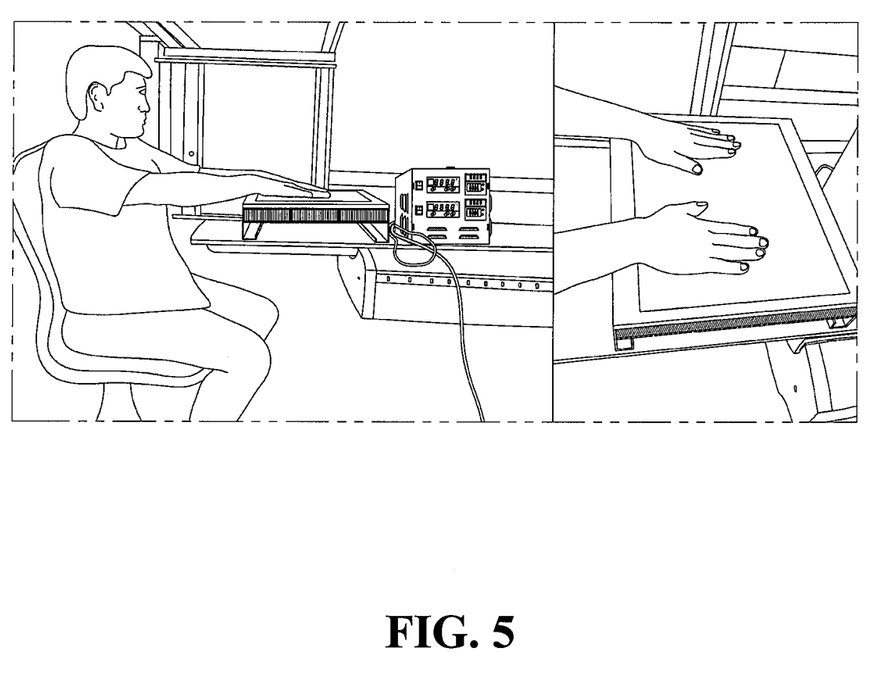
FIG. 5 is a view illustrating a usage state of the cold and hot thermal treatment device according to the present disclosure.
Figure 6:
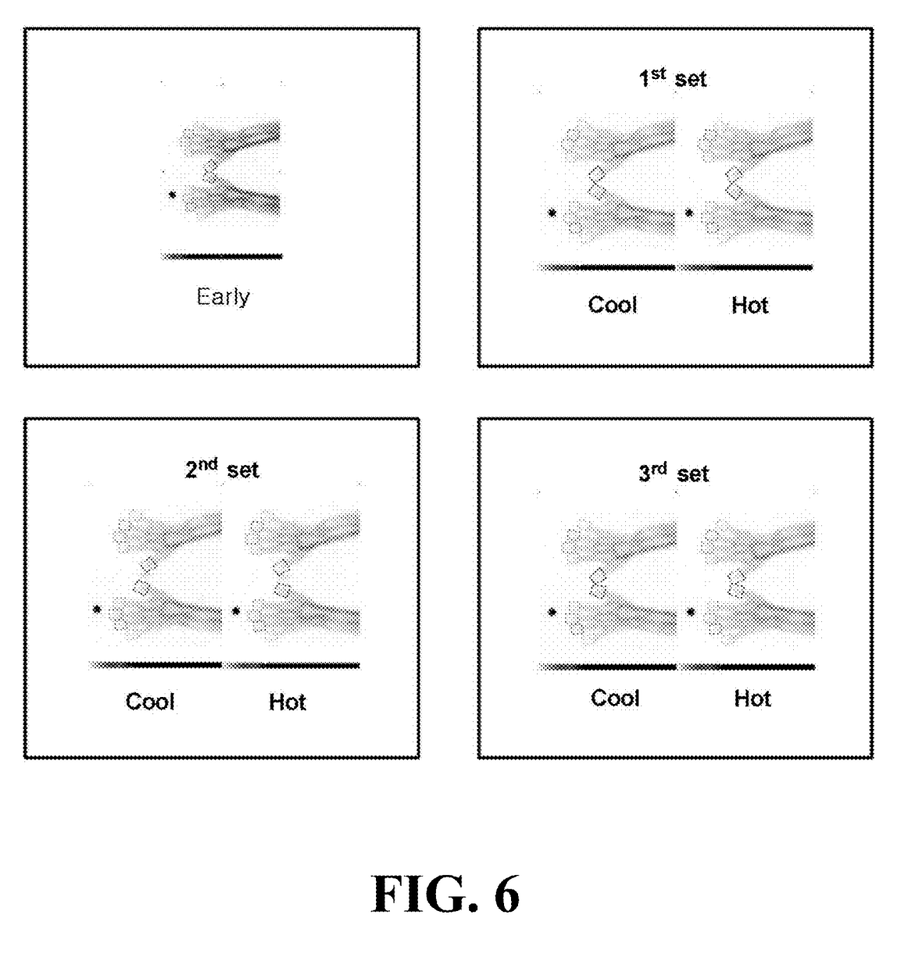
FIG. 6 is a view illustrating a resultant image obtained by performing a test using the cold and hot thermal treatment device according to the present disclosure.

FIG. 5 is a view illustrating a usage state of the cold and hot thermal treatment device according to the present disclosure, and FIG. 6 is a view illustrating a resultant image obtained by performing a test using the cold and hot thermal treatment device according to the present disclosure.

As illustrated in FIGS. 5 and 6, a test process using the cold and hot thermal treatment device 100 according to the present disclosure will be described below.

First, the purpose of a test is to observe the amount of blood which is changed according to repetitive cold and hot heat stimulation.

In the test, a 99mTC-RBC labeling method, which is one of nuclear medicine testing methods, is used. The method is a testing method of replacing an iron component contained in erythrocytes in blood with 99mTc (technetium) corresponding to an isotope which can be traced using nuclear medicine equipment.

In the testing method, the nuclear medicine equipment used to trace the isotope is SPECT.

Figure 7:
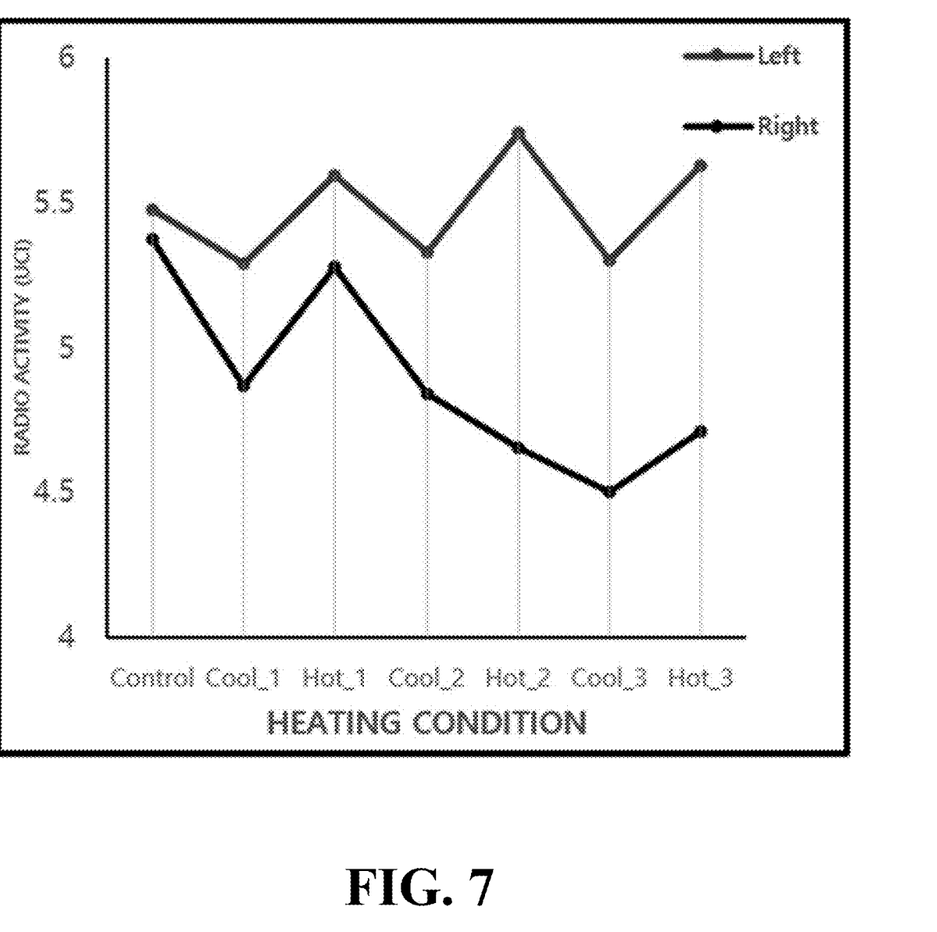
FIG. 7 is a view illustrating a conclusion derived according to the test result of FIG. 6.

FIG. 7 is a view illustrating a conclusion derived according to the test result of FIG. 6. As illustrated in FIG. 7, a PMOD corresponding to a medical image quantification program is used to derive the conclusion.

The purpose of a test is to observe the amount of blood which is changed according to repetitive cold and hot heat stimulation. How artificial temperature transfer affects the volume of blood is identified and whether a blood vessel is reacted according to a given stimulus is identified by measuring a change in the amount of blood at the target portion through a comparison between a result obtained when the stimulus is given, and a result obtained when the stimulus is not given.

As illustrated in FIG. 6, in a state in which a region of interesting (ROI) is set at ends of fingers of right and left hands, the amount of blood during cold heat stimulus and the amount of blood during hot heat stimulus are examined in a fragmentary manner.

Figure 8:
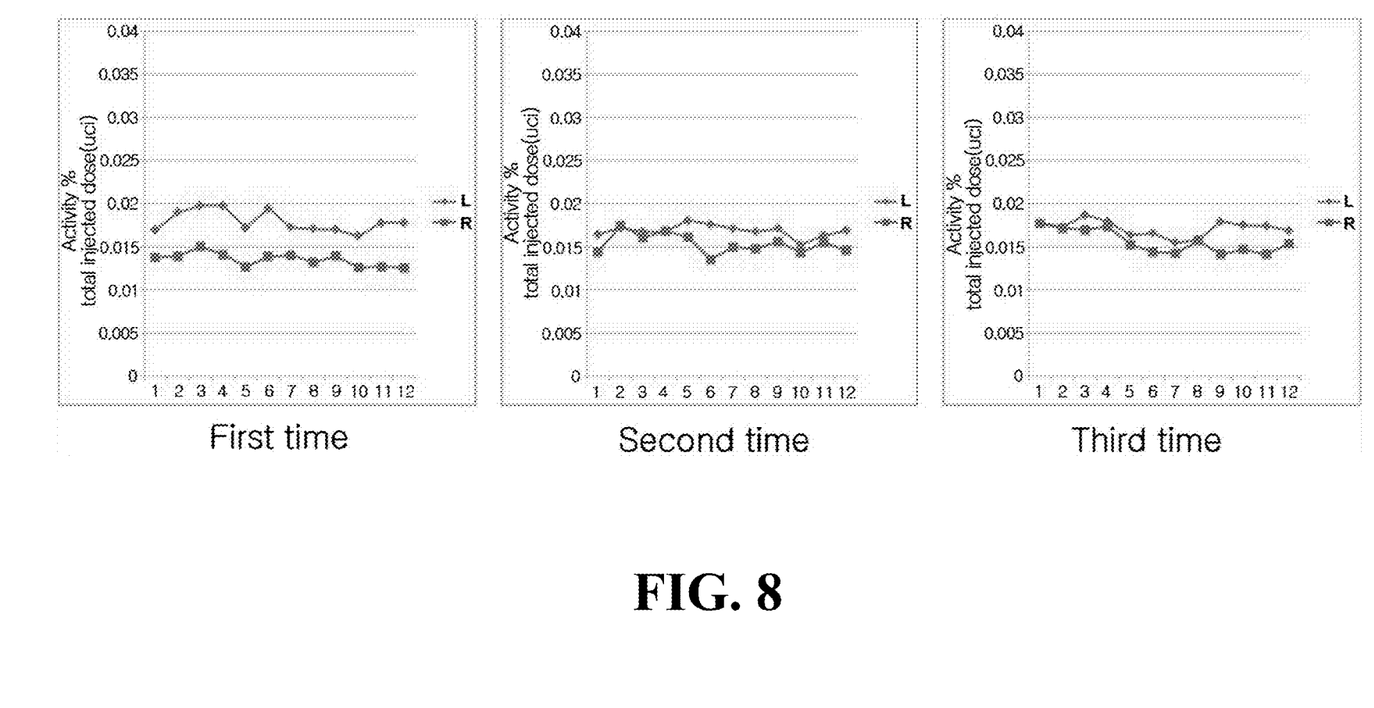
FIG. 8 is a view illustrating an example where temperature responsiveness of a blood vessel is recovered when a repetitive stimulus test is progressed.

FIG. 8 is a graph depicting a result derived from an analysis example of FIG. 7.

Unlike the analysis example of FIG. 7, FIG. 8 is a graph depicting a result in which a repeated and sustained stimulus recovers temperature responsiveness of blood vessels. In the graph, when a stimulus is performed once, there is a difference between temperature responsiveness of both hands. However, as the number of times of stimuli increases, a hand having low temperature responsiveness is gradually recovered.

Figure 9:
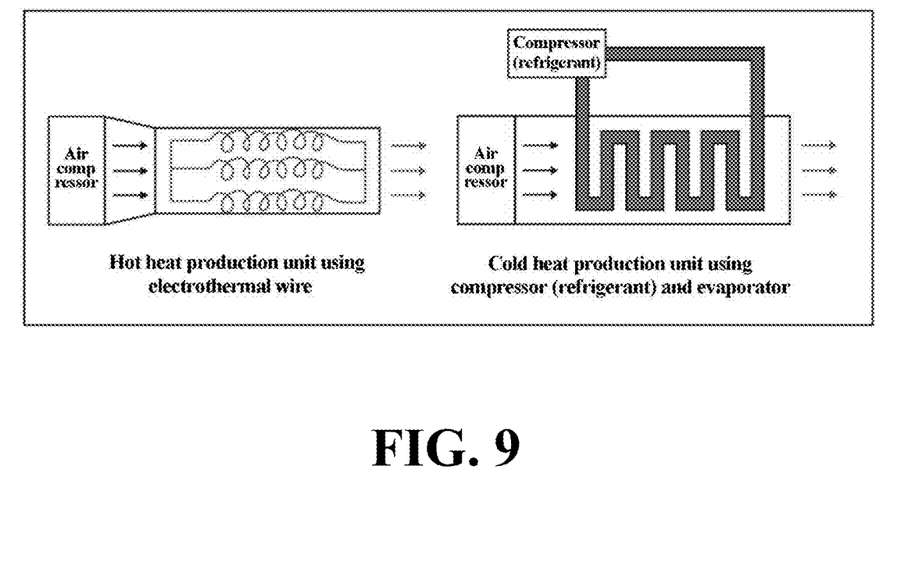
FIG. 9 is a conceptual view illustrating a hot heat production unit using an electrothermal wire and a cold heat production unit using a compressor and an evaporator according to the present disclosure.
Figure 10:
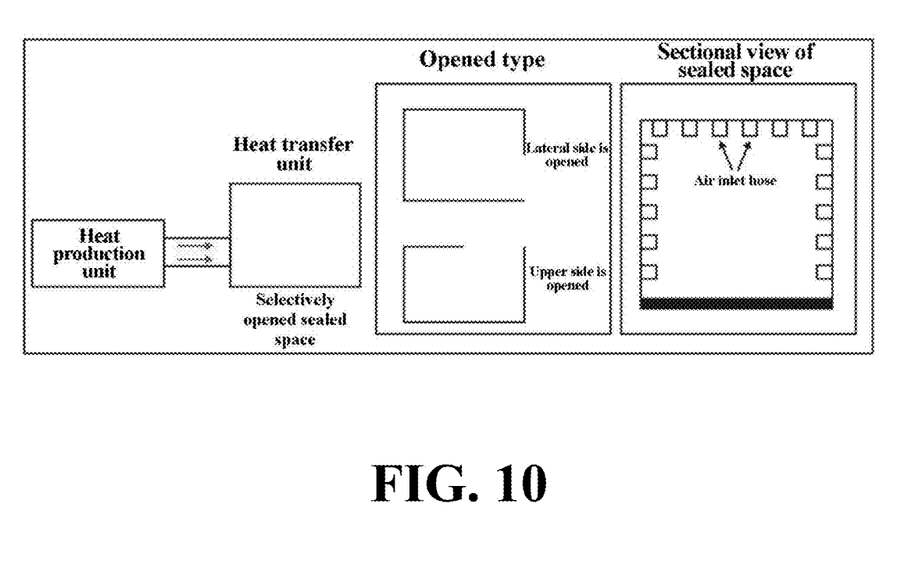
FIG. 10 is a conceptual view illustrating various types of heat transfer units configured to transfer heat produced by the heat production units of FIG. 9.
Figure 11:
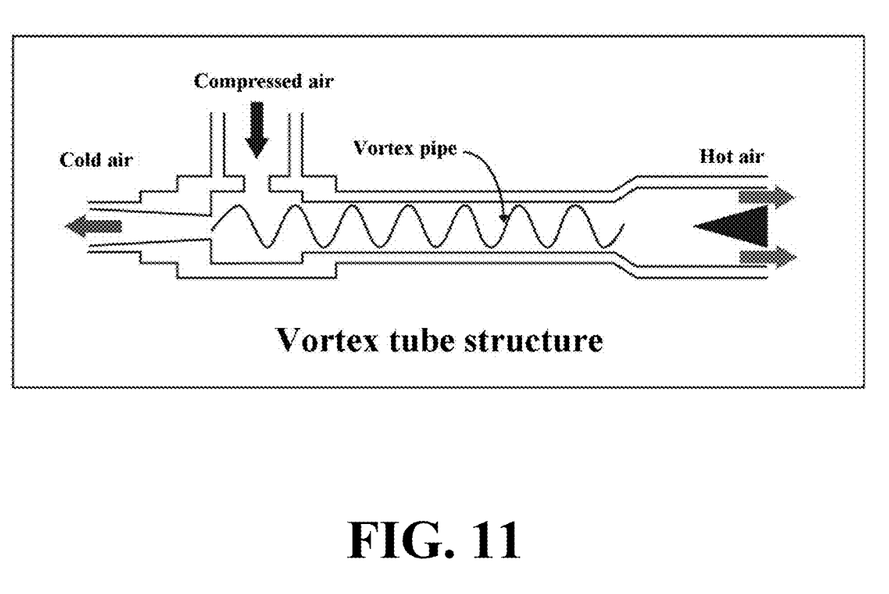
FIG. 11 is a conceptual view illustrating a heat production unit using a vortex tube according to the present disclosure.

Meanwhile, FIG. 9 is a conceptual view illustrating a hot heat production unit using an electrothermal wire and a cold-heat production unit using a compressor and an evaporator according to the present disclosure, FIG. 10 is a conceptual view illustrating various types of heat transfer units configured to transfer heat produced by the heat production units of FIG. 9, and FIG. 11 is a conceptual view illustrating a heat production unit using a vortex tube according to the present disclosure.

As illustrated in FIGS. 9 to 11, the heat production unit 10 is configured to produce hot heat and cold heat. For example, the hot heat produced by the heat production unit 10 is produced by any one of a thermoelectric element, an electrothermal wire, and a vortex tube, and the cold heat is produced by any one of the thermoelectric element, a compressor, a refrigerant, and an evaporator, liquid nitrogen and dry ice, and the vortex tube.

A heat transfer medium of the heat transfer unit 30 may be changed according to a constituent material of the heat production unit 10. For example, the heat transfer unit 30 may be a box-shaped or cover-shaped sealed space part which is selectively opened and in which a part or a lower half part of a human body is accommodated.

As illustrated in FIGS. 9 and 10, the hot heat of the heat production unit 10 is produced through the electrothermal wire (coil) that generates heat when a current flows therethrough and an air compressor configured to produce compressed air corresponding to a medium through which the produced heat is transferred to the heat transfer unit 30. The cold heat of the heat production unit 10 is produced through the refrigerant, the compressor, and the evaporator. The hot heat and the cold heat are transferred to the heat transfer unit 30 that is a separate space isolated (selectively opened) from the outside, using the compressed air, to change or maintain the temperature of the space.

Here, an air inlet hose through which the heat produced by the heat production unit 10 may be introduced is formed in the heat transfer unit 30, and an application part is determined as a hand, a foot, and a lower half part depending on the size and the shape of a blocked space. Further, various forms such as a box made of wood or steel and socks and gloves made of thick cloth may be applied to the heat transfer unit 30.

The cold heat produced by the heat production unit 10 may be produced through a structure including the compressor, the refrigerant, and the evaporator, and the produced cold heat may be also produced using liquid nitrogen and dry ice as alternatives of the compressor, the refrigerant, and the evaporator.

FIG. 11 is a view illustrating a configuration of a heat production unit using a vortex tube according to the present disclosure, and the hot heat and the cold heat may be produced using a vortex tube having a vortex pipe. That is, the vortex tube configured to simultaneously produce the hot heat and the cold heat using the compressed air is a device configured to generate a whirling vortex that rotates at about one million RPM by an internal vortex pipe and to separately discharge cold wind and hot wind using air pressure. The vortex tube is mainly used when local cooling is performed in a factory.

Meanwhile, it should be noted while the cold and hot thermal treatment device according to the present disclosure is manufactured that the device is a system that may provide gradual temperature increase and decrease, and at which speed the temperature increase and decrease are provided, during which period a maximum temperature and a minimum temperature are provided, and the maximum temperature and the minimum temperature are determined medically. Thus, provided is a system that repeatedly provides a change in a temperature as a change in an external environment to determine maintenance of vascular reactivity and to recover the vascular reactivity, as a component that may set an increase/decrease rate of a temperature, the maximum temperature, and the minimum temperature is necessarily provided.

As described above, when a disease is diagnosed by identifying whether the vascular reactivity is maintained in the corresponding hand or foot or is broken, the device may be used as a stimulus source. Further, to recover the vascular reactivity, a temperature is repeatedly changed between a cold state and a hot state so that a vascular exercise to a stimulus is consistently performed. Accordingly, the disease may be treated through rehabilitation for the vascular reactivity.

The above description is a merely illustrative description of the technical spirit of the present disclosure, and various modifications, changes, and substitutions may be made by those skilled in the art to which the present disclosure pertains without departing from the essential feature of the present disclosure. Thus, the embodiments and the accompanying drawings that are disclosed in the present disclosure are not for limiting but for describing the technical spirit of the present disclosure, and the scope of the technical spirit of the present disclosure is not limited by the embodiments and the accompanying drawings. The protection scope of the present disclosure should be interpreted by the appended claims and all the technical spirit corresponding to the equivalents thereof should be interpreted to be included in the scope of a right of the present disclosure.

The invention claimed is:

1. A cold and hot thermal treatment device comprising:
a heat production unit configured to produce hot heat and cold heat;
a power source electrically connected to the heat production unit to supply electric power;
a heat transfer unit configured to transfer heat produced by the heat production unit to a target portion that is in contact with a human body; and
a controller configured to control the heat production unit to repeatedly and alternately generate the hot heat and the cold heat according to a set period, to perform a control such that a temperature is gradually increased at a first constant rate to a predetermined maximum temperature and is gradually decreased at a second constant rate to a predetermined minimum temperature, and to perform a control such that after the temperature reaches the maximum temperature and the minimum temperature, the temperature is maintained for a predetermined time period.

2. The cold and hot thermal treatment device of claim 1 further comprising a digital thermometer and a timer.

3. The cold and hot thermal treatment device of claim 2 further comprising an insulator in a heat transfer passage provided between the heat production unit and the heat transfer unit.

4. The cold and hot thermal treatment device of claim 3 further comprising a temperature measuring sensor at a distal end of the heat transfer unit, which is in contact with a human body.

5. The cold and hot thermal treatment device of claim 4, wherein the hot heat produced by the heat production unit is produced by a device selected from the group consisting of a thermoelectric element, an electrothermal wire, and a vortex tube.

6. The cold and hot thermal treatment device of claim 4, wherein the cold heat produced by the heat production unit is produced by a device selected from the group consisting of a compressor, a refrigerant, an evaporator, liquid nitrogen, dry ice, and a vortex tube.

7. The cold and hot thermal treatment device of claim 4, wherein the heat transfer unit is one of a box-shaped sealed space part and cover-shaped sealed space part, which is selectively opened, and in which a part of a human body is accommodated.

8. The cold and hot thermal treatment device of claim 1, wherein an insulator is installed in a heat transfer passage provided between the heat production unit and the heat transfer unit.

9. The cold and hot thermal treatment device of claim 8, wherein a temperature measuring sensor is further installed at a distal end of the heat transfer unit, which is in contact with a human body.

10. The cold and hot thermal treatment device of claim 9, wherein the hot heat produced by the heat production unit is produced by any one of a thermoelectric element, an electrothermal wire, and a vortex tube.

11. The cold and hot thermal treatment device of claim 9, wherein the cold heat produced by the heat production unit is produced by any one of a compressor, a refrigerant, and an evaporator, and liquid nitrogen and dry ice, and a vortex tube.

12. The cold and hot thermal treatment device of claim 9, wherein the heat transfer unit is a box-shaped or cover-shaped sealed space part which is selectively opened and in which a part or a lower half part of a human body is accommodated.

13. A thermal treatment device comprising:
a thermal production unit;
a power source communicative with the thermal production unit;
a thermal transfer unit configured to transfer thermal energy from the thermal production unit to a target; and
a controller configured to control the thermal production unit to generate temperatures between a minimum and maximum temperature;
wherein when the thermal production unit reaches the maximum temperature, the maximum temperature is maintained for a first time period;
wherein when the thermal production unit reaches the minimum temperature, the minimum temperature is maintained for a second time period;
wherein during a cycle of lowering the temperature of the thermal production unit from the maximum temperature to the minimum temperature, the temperature is lowered at a first constant rate; and
wherein during a cycle of raising the temperature of the thermal production unit from the minimum temperature to the maximum temperature, the temperature is raised at a second constant rate.

14. The thermal treatment device of claim 13, wherein the cycles of lowering and raising the temperature are repeatedly and alternately generated;
wherein the first constant rate and the second constant rate are substantially the same; and
wherein the first time period and the second time period are substantially the same.

15. The thermal treatment device of claim 14 further comprising:
a digital thermometer; and
a timer.

16. The thermal treatment device of claim 14 further comprising:
an insulator positioned in a thermal transfer passage provided between the thermal production unit and the thermal transfer unit; and
a thermal sensor positioned at a distal end of the thermal transfer unit.

17. The thermal treatment device of claim 14, wherein the thermal transfer unit has a shape selected from the consisting of a box-shape and cover-shape;
wherein the shape is a sealed space part that is selectively opened; and
wherein a part of a human body is accommodated.

* * * * *